United States Patent [19]
Lin

[11] Patent Number: 5,964,728
[45] Date of Patent: Oct. 12, 1999

[54] SYNCHRONOUS VITREOUS LAVAGE DEVICE FOR OPHTHALMOLOGY AND AN OPHTHALMOLOGIC LAVAGING SYSTEM USING THE SAME

[76] Inventor: Po-Kang Lin, 2F, No. 283-1 Chng Tsun Rd., Taipei, Taiwan

[21] Appl. No.: 08/940,220

[22] Filed: Sep. 30, 1997

[51] Int. Cl.[6] .................................................. A61M 1/00
[52] U.S. Cl. .............................. 604/30; 604/38; 604/121; 604/155
[58] Field of Search .................................. 604/27, 30–31, 604/33, 35–36, 38, 54, 173, 181, 183, 294, 310–311, 121, 155, 119

[56] References Cited

U.S. PATENT DOCUMENTS 5,860,949  1/1999  Chen ........................................... 604/35

*Primary Examiner*—Wynn Wood Coggins
*Assistant Examiner*—Loan H. Thanh

[57] ABSTRACT

A synchronous vitreous lavage device for ophthalmology includes a platform, a pair of main and auxiliary supporters, a pair of guiding arms, a movable seat and a pair of clamps. When the movable seat moves in the direction of the guiding arms, the lavage device simultaneously drains bloody water from an eyeball and injects lavage water into the eyeball by means of two syringes. The bloody water in the eyeball can be easily removed from the eyeball at a cheap cost. An ophthalmologic lavaging system is formed by connecting two regulating syringes through two three-way valves to the lavage device.

2 Claims, 5 Drawing Sheets

SYNCHRONOUS VITREOUS LAVAGE DEVICE FOR OPHTHALMOLOGY AND AN OPHTHALMOLOGIC LAVAGING SYSTEM USING THE SAME

FIELD OF THE INVENTION

This invention relates to a synchronous vitreous lavage device for ophthalmology, particularly to a lavage device which drains the bloody water out of a patient eyeball and simultaneously injects the lavage water into the eyeball after an ophthalmology operation has been performed on the patient. During the lavaging, the pressure in the eyeball is under good control and the lavaging operation is easily done with no bloody water remaining in the eyeball. This invention also relates to an ophthalmologic lavaging system using the above lavage device.

BACKGROUND OF THE INVENTION

After an ophthalmological surgical operation, such as retina surgical operation, has been performed on a patient, some bloody water remains within the patient eyeball and should be removed from the eyeball. Conventional method of removing the bloody water is to perform an additional ophthalmological surgical operation. The conventional method is costly, dangerous and time-consuming.

SUMMARY OF THE INVENTION

It is an object of the present invention to provide a synchronous vitreous lavage device for ophthalmology. After two syringes are mounted on the lavage device and the flanges of the syringe pistons are fixed on the movable seat, when the movable seat moves along the two guiding axes, one of the syringes absorbs the bloody water from the eyeball into it, and the other syringe simultaneously injects lavaging water into the eyeball. The absorption and injection of the two syringes are synchronously and isovolemicaly. Thus in the present invention it becomes easy, accurate and convenient to remove the bloody water.

It is another object of the present invention to provide an ophthalmologic lavaging system which comprises the above synchronous lavage device, a plurality of syringes, a plurality of three-way valves, a plurality of regulating syringes, a plurality of pipes and a plurality of syringe needles.

BRIEF DESCRIPTIONS OF THE DRAWINGS

DETAILED DESCRIPTION OF THE INVENTION

Figure 1:
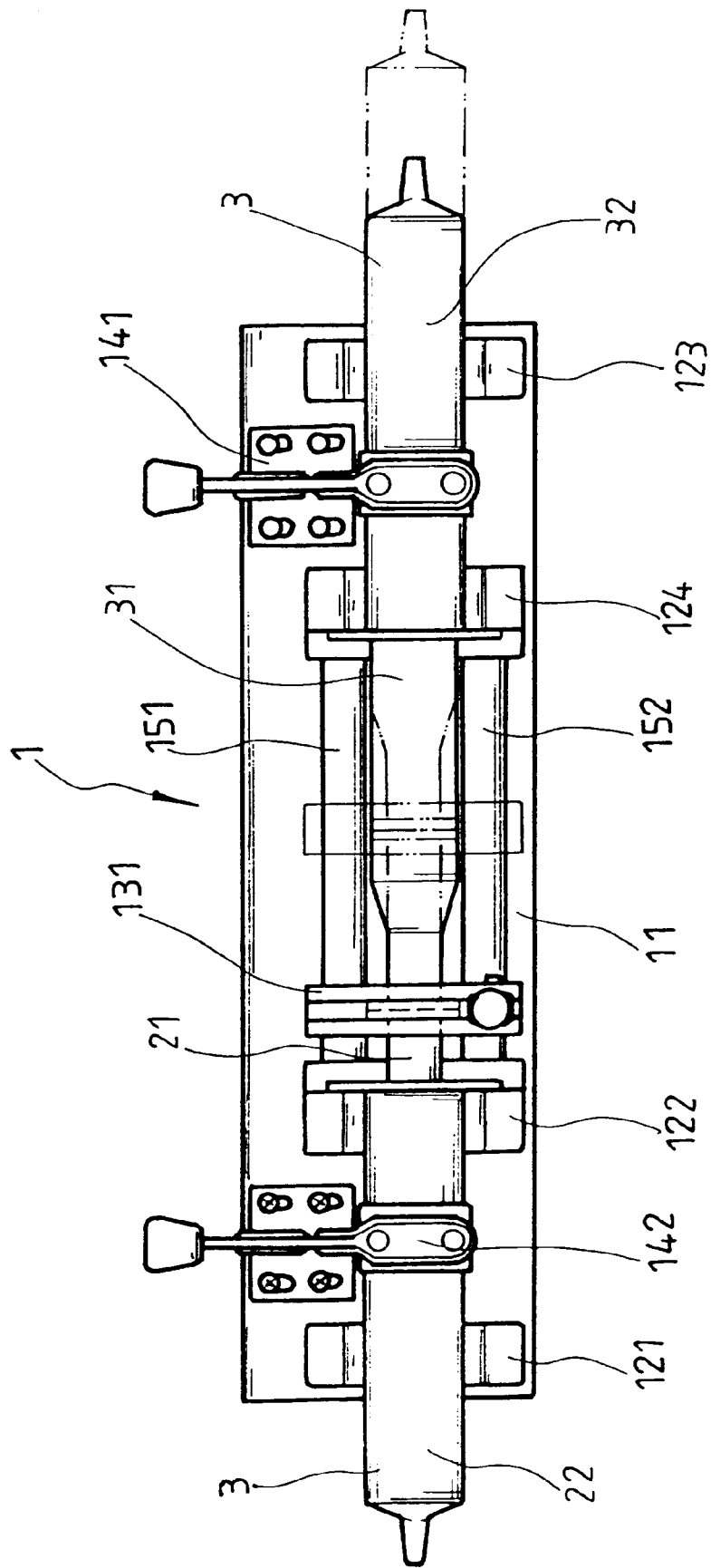
FIG. 1 is a top view of the synchronous vitreous lavage device of the present invention.
Figure 2:
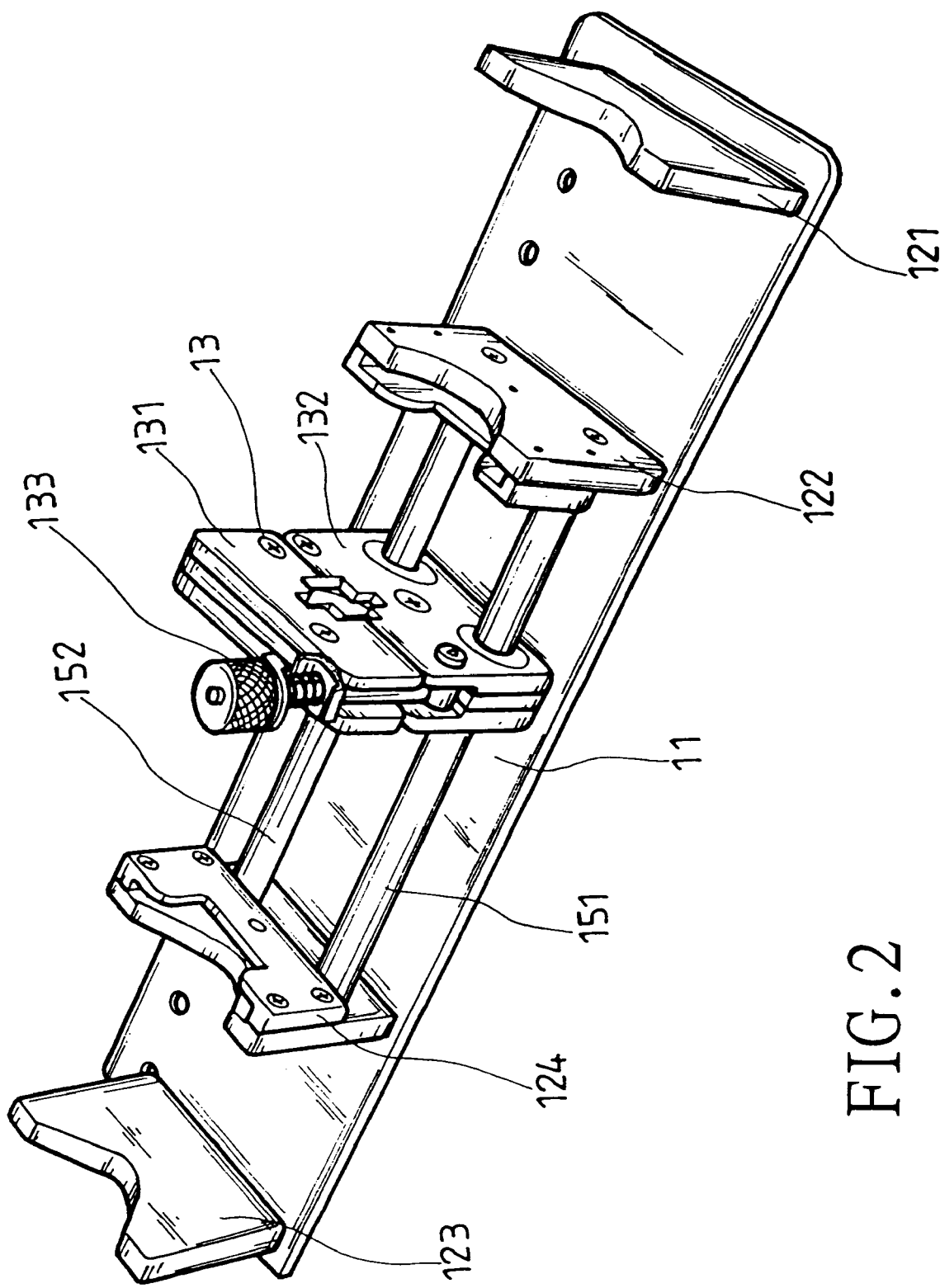
FIG. 2 is a isometric view of the synchronous vitreous lavage device of the present invention.

Please see FIGS. 1 to 5, a synchronous vitreous lavage device for ophthalmology 1 of the present invention simultaneously drains bloody water from the eyeball 7 of a patient and injects lavage water into the eyeball 7 by means of two syringes. The device comprises: a platform 11, a pair of main and auxiliary supporters (121,122), (123,124), two guiding arms 151,152, a movable seat 13, and two clamps 141,142.

The platform 11 is used to support all other elements of the lavage device 1.

The main and auxiliary supporters 121,122,123,124 which are fixed on the platform 11, are used to support the syringes 2,3.

The guiding arms 151,152 which extend through the movable seat 13 are used to guide the movable seat 13 to move along the arms.

The movable seat 13 which moves along the guiding arm 151,152 and onto which one piston end of each syringe is fixed. In one embodiment of the present invention, a fixing slot 134 is formed in the movable seat 13. The flanges 23, 33 of the syringes are engaged to the fixing slot 134. Thus, when the movable seat 13 moves along the extending direction of the guiding arms 151,152, the first and second pistons 21,31 move along the guiding arms 151,152 in the same direction. Because the first and second syringe 2,3 are placed with the flanges 23,33, which are fixed together, one of the syringe 3 absorbs bloody water from the eyeball 7 and the other syringe 2 injects lavage water into the eyeball 7 isovolemically. Although in the embodiment shown in FIG. 4, the two flanges 23,33 are fixed in the fixing slot 134 of the movable seat 13, many modifications can be made without departing from the principle of the invention. For example, the two flanges can be fixed to the movable seat by two seat clamps. It is also possible to use flange clamps to clamp the two flanges together directly.

The clamps 141,142 are used to fix the syringe 2,3 on the supporters.

Figure 4:
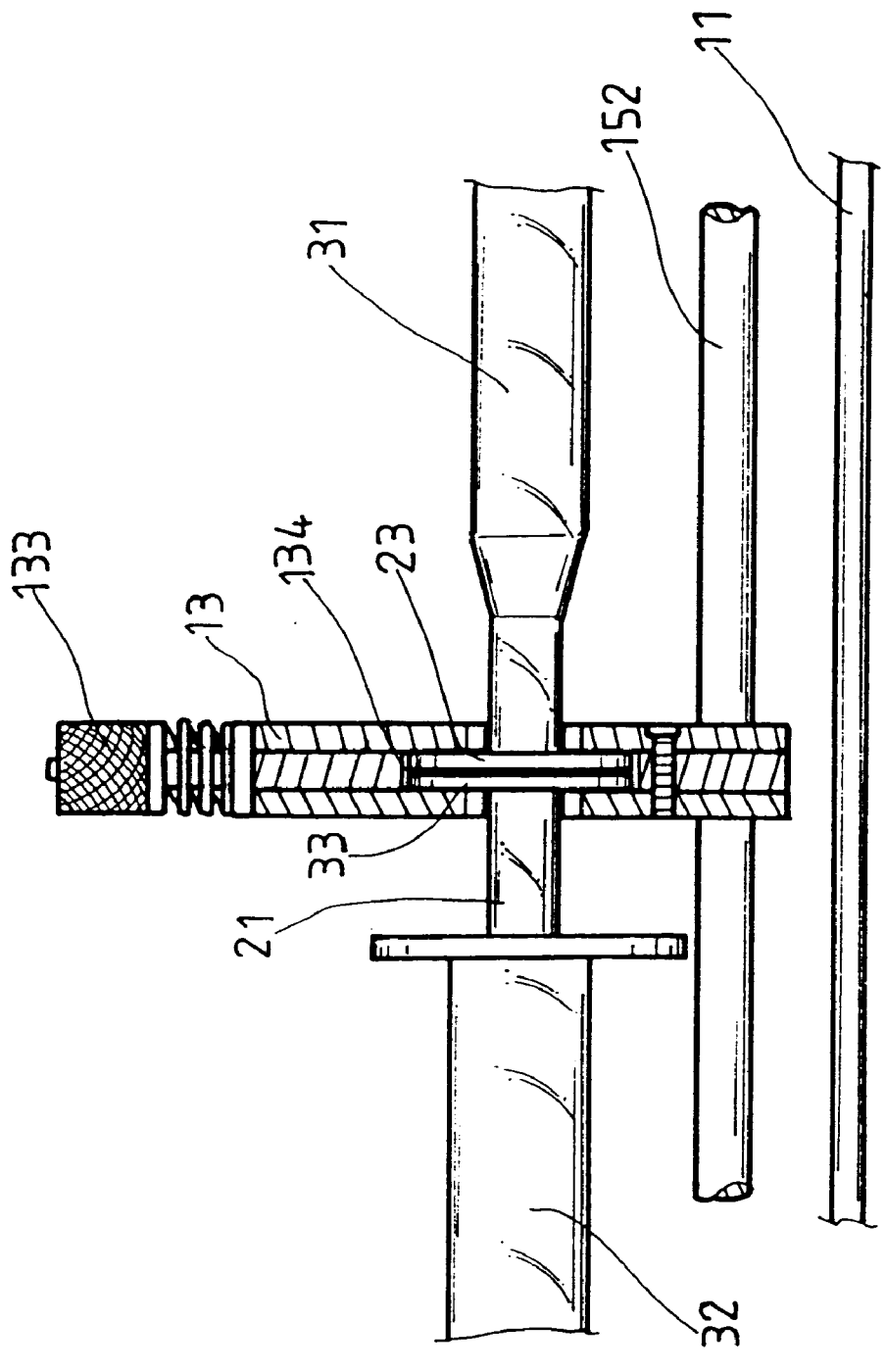
FIG. 4 is a cross-section view of the movable seat of the present invention.
Figure 5:
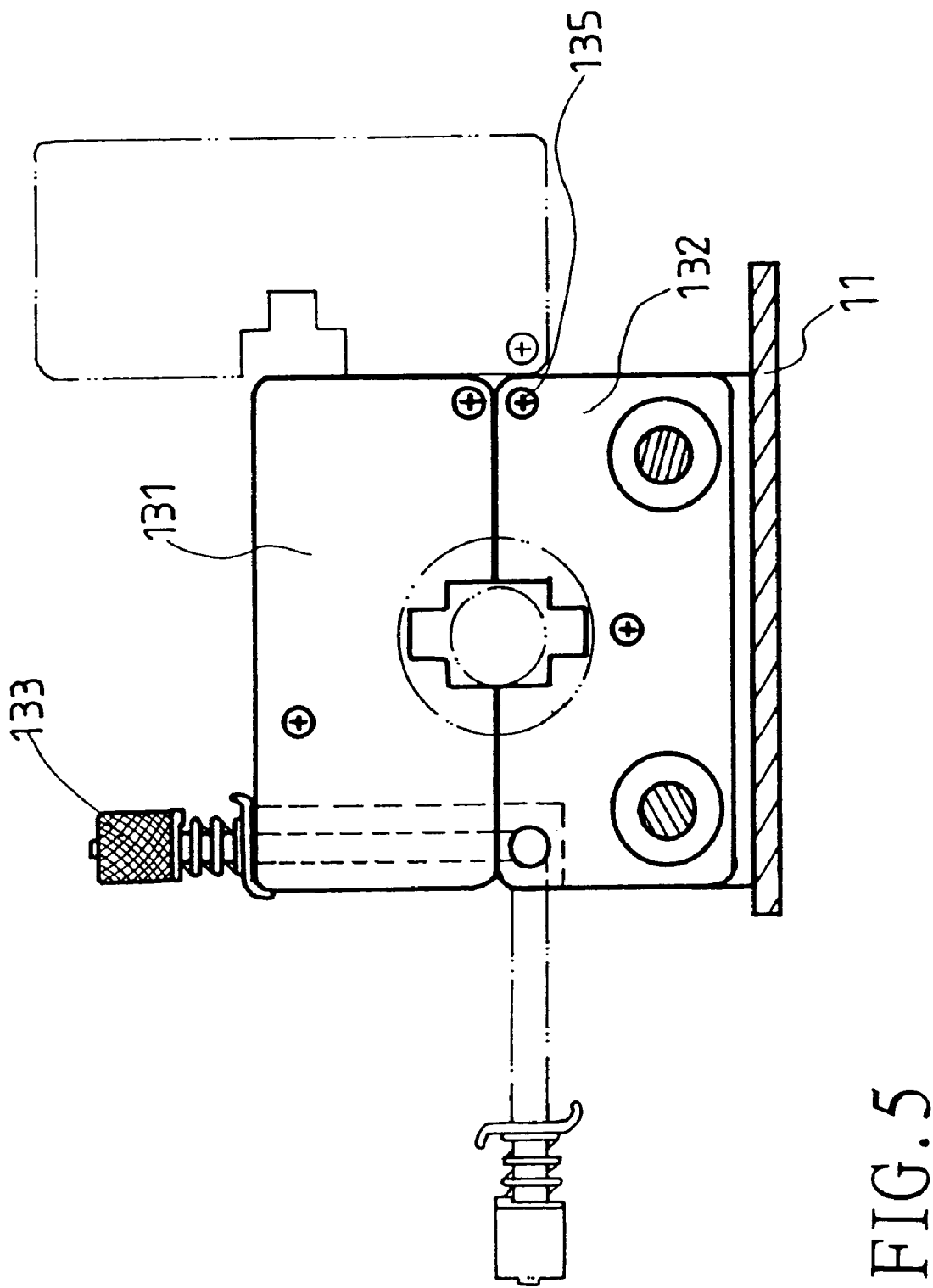
FIG. 5 is a schematic view of the movable seat of the present invention.

In FIG. 4, the flanges 23,33 of the pistons 21, 31 are inserted into the fixing slot 134 of the movable seat 13. The movable seat 13 comprises an upper seat body 131, a lower seat body 132, and a lock 133 which is used to lock the upper seat body 131 and the lower seat body 132 together as shown in FIG. 5. The upper seat body 131 is manufactured in such a way that it can rotate clockwise about a pivot axis 135. As shown in FIG. 5, a screw at a connection point located at the upper right corner of the lower seat body 132 serves as the pivot axis 135. The dotted line shape on the right side of FIG. 5 shows the place where the upper seat body 131 will be positioned after being rotated.

Figure 3:
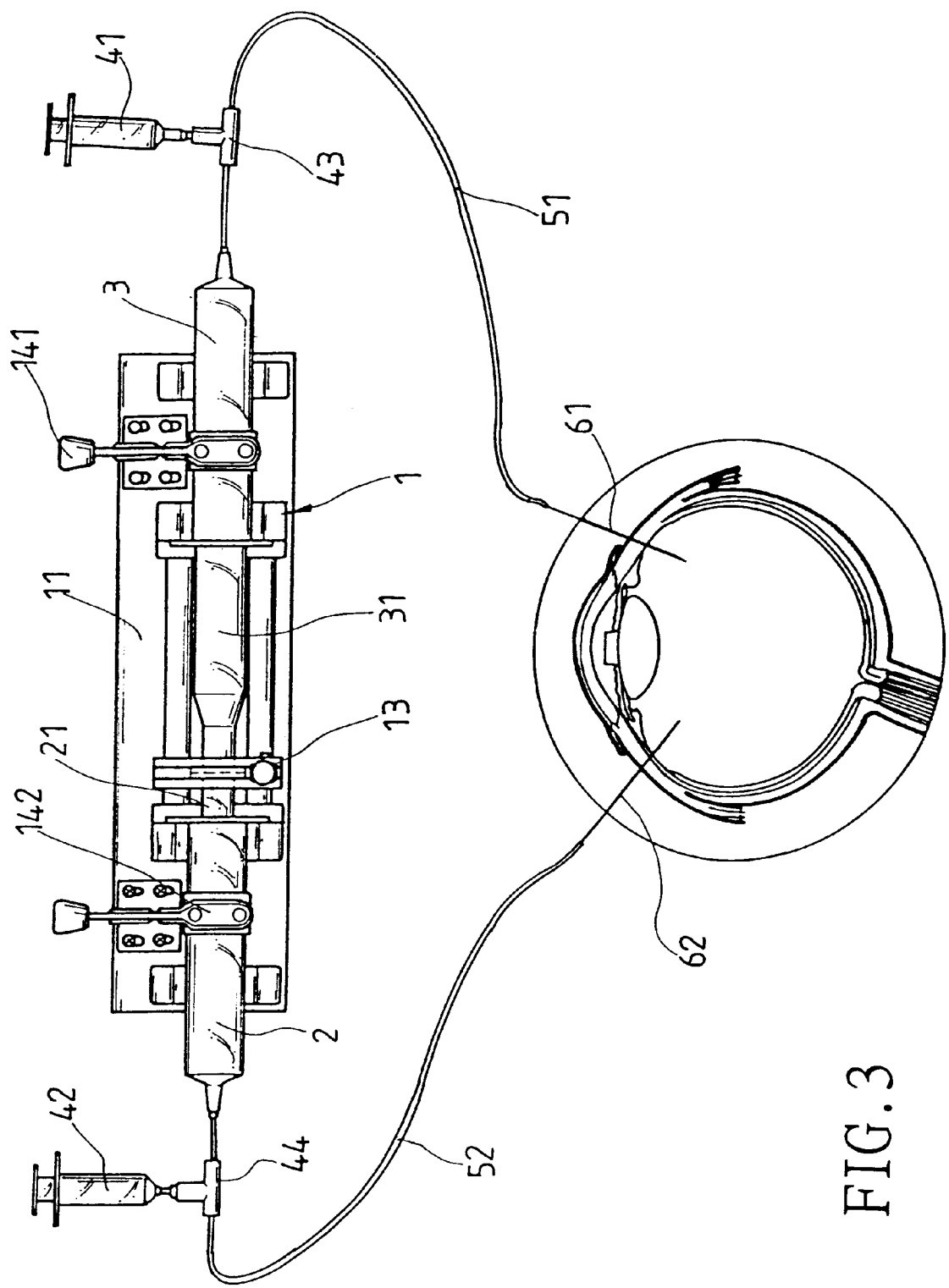
FIG. 3 is a schematic view of the ophthalmologic lavaging system of the present invention.

Please see FIG. 3 which is a schematic view of the ophthalmologic lavaging system, comprising: the above synchronous vitreous lavage device, two syringes 2,3, two three-way valves 43,44, two regulating syringes 41,42, two pipes 51,52, and two syringe needles 61,62.

The first ends of the three-way valves 43,44 are connected to the syringes 2,3 respectively, the second ends of the three-way valves 43,44 are connected to the regulating syringes 41,42 respectively, and the third ends of the three-way valves 43,44 are connected to the first ends of tubes 51,52. The second ends of the tubes 51,52 are connected to the first ends of two syringe needles 61,62. The second ends of the syringe needles 61,62 are inserted into an eyeball 7 as shown in FIG. 3. We assume that in the hollow barrel 22 is the lavage water to be injected into the eyeball 7 and that in the hollow barrel 32 is the bloody water to be absorbed out of the eyeball. When the movable seat 13 moves toward the right side, the piston 21 pushes the lavage water enter into the eyeball 7 via the three-way valve 43, the pipe 51, and the needle 61. The piston 31 absorbs the bloody water in the eyeball 7 via the needle 62, the pipe 52, and the three-way valve 44.

The function of the regulating syringes 41,42 is to regulate the amount of the bloody and lavage water in the eyeball, therefore, the pressure in the eyeball 7 is in normal range, and the shape of the eyeball 7 can be retained. Please see FIG. 3.

We claim:

1. An ophthalmologic lavaging system comprising:

a platform having a plurality of supporters fixed on said platform; a plurality of clamps on said supporters; a plurality of syringes each having a piston end fixed within said clamps; at least one guiding arm on said platform placed between said supporters; a movable seat connected to said at least one guiding arm; wherein said piston ends of said syringes are fixed onto said movable seat;

a plurality of three-way valves wherein each of the three-way valves further has a first end connected to a respective one of said syringes, said three-way valves each further having a second end connected to a tube and a third end connected to a regulating syringe; each of said tubes further having a syringe needle connected to an end thereof;

and wherein one of the plurality of syringes comprise a first syringe for draining bloody water from an eyeball of a patient and a second syringe for injecting lavage water into the eyeball simultaneously through said syringe needles when said movable seat is moved along said at least one guiding arm, and said regulating syringes regulate the amount of the bloody water and the lavage water for maintaining pressure in the eyeball in a normal range.

2. The ophthalmologic lavaging system as claimed in claim 1, wherein said piston ends have a flange, said movable seat has a fixing slot and each of said flanges of said piston ends is engaged and fixed in said fixing slot.

* * * * *